United States Patent [19]
Baraka

[11] Patent Number: 6,042,834
[45] Date of Patent: Mar. 28, 2000

[54] HERBAL COMPOSITION FOR DIABETES AND METHOD OF TREATMENT

[76] Inventor: Mohamed Wasif Baraka, P.O. Box 3852, #22039, Al-Salmiya, Kuwait

[21] Appl. No.: 09/095,306

[22] Filed: Jun. 10, 1998

Related U.S. Application Data

[63] Continuation-in-part of application No. 08/790,607, Jan. 29, 1997, abandoned.

[51] Int. Cl.⁷ .................................................. A61N 65/00
[52] U.S. Cl. ...................... 424/195.1; 425/451; 425/489; 514/866
[58] Field of Search ................................ 424/195.1, 451, 424/489; 514/866

[56] References Cited

U.S. PATENT DOCUMENTS

| | | | |
|---|---|---|---|
| 5,470,879 | 11/1995 | Sauvaire et al. | 514/561 |
| 5,482,711 | 1/1996 | Medenica | 424/195.1 |
| 5,866,555 | 2/1999 | Bell et al. | 514/60 |
| 5,886,029 | 3/1999 | Dhaliwal | 514/456 |

*Primary Examiner*—Leon B. Lankford, Jr.
*Assistant Examiner*—Christopher R. Tate
*Attorney, Agent, or Firm*—Brenda L. Speer

[57] ABSTRACT

An herbal composition for the treatment of diabetes, comprising 15 percent by weight of dried, powdered seeds of *Trigonella foenum-graecum*; 23 percent by weight of dried, powdered seeds of *Nigella sativa*; 10 percent by weight of dried, powdered leaves of *Origanum vulgare*; 10 percent by weight of dried, powdered sap of *Rosmarinus officinalis*; 15 percent by weight of dried, powdered beans of *Lupinus termis*; 12 percent by weight of dried, powdered black leaves of *Lawsonia inermis*; and 15 percent by weight of dried, powdered seeds of *Foeniculum vulgare*. The herbal composition may be administered in non-encapsulated powder form or in capsule form. A method of treatment for diabetes using the herbal composition comprises monitoring a diabetic patient's blood sugar level; administering to the patient the herbal composition in an amount of about 9 g per day for at least about 60 days until such date as the patient's blood sugar level achieves and maintains normalcy; administering to the patient the herbal composition in the amount of about 6 g per day for about another 7 days; administering to a patient the herbal composition in the amount of about 3 g per day for about another 14 days; and discontinuing administration, or, alternatively, continuing administration of the herbal composition as necessary for the patient at about less than or equal to 3 g per day of the herbal composition.

7 Claims, No Drawings

HERBAL COMPOSITION FOR DIABETES AND METHOD OF TREATMENT

RELATED APPLICATION

This application is a continuation-in-part application of Ser. No. 08/790,607, entitled "Herbal Remedy for Diabetes and Method of Treatment", filed Jan. 29, 1997, now abandoned.

FIELD OF THE INVENTION

The invention generally relates to an herbal composition for diabetes and a method of treatment for diabetes using the herbal composition.

BACKGROUND OF THE INVENTION

Diabetes has been a known medical problem for some time. Treatment for diabetes typically requires the regular administration of insulin to the patient, either orally or by injection. Such a treatment of diabetes is a life-long course of treatment for the afflicted patient. For many patients, insulin injection is an unpleasant process. Also, the need for daily injections of insulin is hard on the patient's veins. Insulin treatment is costly and it is only a temporary reliever of diabetic symptoms. Continued treatment is necessary in order to control the disease. Therefore, there is a need for a remedy and treatment for diabetes which is permanent, not temporary, and which is easily administered to or by the patient.

SUMMARY OF THE INVENTION

An herbal composition for the treatment of diabetes, comprising 15 percent by weight of dried, powdered seeds of *Trigonella foenum-graecum*, 23 percent by weight of dried, powdered seeds of *Nigella sativa*, 10 percent by weight of dried, powdered leaves of *Origanum vulgare*, 10 percent by weight of dried, powdered sap of *Rosmarinus officinalis*, 15 percent by weight of dried, powdered beans of *Lupinus termis*, 12 percent by weight of dried, powdered black leaves of *Lawsonia inermis*, and 15 percent by weight of dried, powdered seeds of *Foeniculum vulgare*. The herbal composition may be administered in non-encapsulated powder form or in capsule form. A method of treatment for diabetes comprising monitoring the patient's blood sugar level; administering to a patient the herbal composition in an amount of 9 g per day for at least 60 days until such date as the patients blood sugar level achieves and maintains normalcy; administering to a patient the herbal composition in the amount of 6 g per day for another 7 days; administering to a patient the herbal composition in the amount of 3 g per day for another 14 days; and discontinuing administration of the herbal composition or continuing administration of the herbal composition as necessary for the patient at about less than or equal to 3 g per day of the herbal composition.

DETAILED DESCRIPTION OF THE INVENTION

The invention is an herbal composition. It is comprised of the herbs *Trigonella foenum-graecum*, *Rosmarinus officinalis*, *Nigella sativa*, *Lupinus termis*, *Lawsonia inermis*, *Origanum vulgare* and *Foeniculum vulgare*.

These plants may be found in various places in the world. Specifically, *Trigonella foenum-graecum* may be found in India, Saudi Arabia and Egypt. *Rosmarinus officinalis* may be found in Saudi Arabia and South Yemen. *Nigella sativa* may be found in Iran, Morocco and Syria. *Lupinus termis* may be found in North America, Egypt, Syria, Australia and Guatemala. *Lawsonia inermis* may be found in Iran, Pakistan, Afghanistan and India. *Origanum vulgare* may be found in Lebanon, Egypt, Syria and Jordan. *Foeniculum vulgare* may be found in Iran and India.

Various parts of each of these different plants are used in the herbal composition. The seeds of *Trigonella foenum-graecum* are used. The seeds of *Nigella sativa* are used. The leaves of *Origanum vulgare* are used. The sap of *Rosmarinus officinalis* is used. The beans of *Lupinus termis* are used. The black leaves of *Lawsonia inermis* are used. The seeds of *Foeniculum vulgare* are used. Each of these different plant products are dried and ground to a powder prior to incorporation into the herbal composition of the invention.

The herbal composition of the invention is preferably prepared in a one kilogram quantity. The kilogram is comprised of 150 g of *Trigonella foenum-graecum*, 230 g of *Nigella sativa*, 100 g of *Origanum vulgare*, 100 g of *Rosmarinus officinalis*, 150 g of *Lupinus termis*, 120 g of *Lawsonia inermis*, and 150 g of *Foeniculum vulgare*. The herbal composition is thoroughly mixed to ensure even distribution of each of the ingredients throughout the one kilogram. Regardless of the weight amounts, the herbal composition should be formulated so that the ingredients comprise a portion of the whole as follows: 15 percent by weight of dried, powdered seeds of *Trigonella foenum-graecum*, 23 percent by weight of dried, powdered seeds of *Nigella sativa*, 10 percent by weight of dried, powdered leaves of *Origanum vulgare*, 10 percent by weight of dried, powdered sap of *Rosmarinus officinalis*, 15 percent by weight of dried, powdered beans of *Lupinus termis*, 12 percent by weight of dried, powdered black leaves of *Lawsonia inermis*, and 15 percent by weight of dried, powdered seeds of *Foeniculum vulgare*.

One kilogram of the herbal composition is approximately a one month supply of the treatment. The treatment is administered in either capsules or may be administered "straight" as the non-encapsulated powdered herbal composition. Either administration method is without any other inert ingredients incorporated with the herbal composition.

When the treatment method with the herbal composition of the invention is begun, if the patient is presently following a course of insulin or other diabetes treatment, then the patient should continue the same in conjunction with the treatment method of the invention. The patient should continue to monitor his or her blood sugar levels in order to determine in conjunction with his or her physician how to taper off administration of insulin once the herbal composition has begun to take effect.

In a healthy person not afflicted by diabetes, blood sugar levels should be from about 70 mg of glucose per deciliter of blood to about 140 mg of glucose per deciliter of blood. In a person suffering from diabetes, he or she must continually take insulin in order to achieve and maintain a normal blood sugar level within the aforementioned range. However, a patient undergoing insulin treatment usually is able to permanently discontinue the same upon completion of a course of treatment with the herbal composition of the invention.

The mechanism by which the herbal composition of the invention operates is not exactly understood. However, it is theorized that the herbal composition stimulates the pancreas to make its own insulin; whereas, in patients suffering from diabetes, the pancreas does not manufacture insulin. The herbs are a stimulant to the pancreas and cause the cells of the pancreas to respond and to recommence production of insulin.

There are no known dangers or side effects associated with treatment with the herbal remedy of the invention. The herbal composition has also produced beneficial effects of improved vision, reduction of gastrointestinal infections, reversal of impotence and relief from constipation in patients receiving the treatment.

At the beginning of the treatment method of the invention, the patient takes about 9 g per day of the herbal composition of the invention. The about 9 g per day is ingested in three separate about 3 g doses administered throughout the day. For instance, a dose preferably may be taken with each of the major meals of the day, breakfast, lunch and dinner. The treatment should be taken in three doses throughout the day, in about 5 hour intervals. The first dose each day is to be taken about 30 to about 45 minutes prior to food ingestion. The second and third doses may be taken prior to, with, or after food ingestion. It is preferred that each of the doses be taken in succession in approximately even intervals of about 5 hours each throughout the day. The second and third doses of the day may be taken with or without food. If the herbal composition is taken in non-encapsulated form, then about 3 g of the herbal composition is approximately equal to about one teaspoon. If the herbal composition is taken in capsule form, then about 1 g of the herbal remedy is equal to about one capsule. The dosage is adapted according to the weight and the metabolism rate of the individual.

With the treatment method of the invention, eventually most patients can discontinue administration of the herbal composition, while some patients may need to continue administration of a very low daily dosage of about less than or equal to 3 g per day. Also, the administration of insulin is no longer required. After treatment has commenced and the blood sugar levels have returned to normal, the administration of insulin is no longer required. However, once the patient's blood sugar level has returned to normal, then the administration of the herbal composition should be continued over a course of an additional three to four weeks. During these additional three to four weeks, the dose of the herbal remedy of the invention is tapered down and eventually discontinued or maintained at a low daily dosage as previously discussed. It has been the experience of the inventor that for most patients following the course of treatment described herein, upon completion they have not needed to resume treatment with either insulin or the herbal composition of the invention.

The treatment period averages from about two to about three months. Within the first 15 days of administration, results will begin to be seen and the blood sugar level will begin to return to normal. A maximum course of administration is about six months, depending upon a patient's weight and metabolism rate.

If the patient is already taking insulin, then the method of treatment takes approximately one month more to take effect than for a patient not already taking insulin and for the pancreas to recommence production of insulin on its own. Thereafter, the patient should take the herbal composition for another several weeks, but at a lower dose. That is, the patient takes about 6 g per day for about the first week of tapering off treatment and then takes about 3 g per day for about the next two weeks of treatment. Then the patient stops treatment. Alternatively, a small percentage of patients may need to continue administration of the herbal remedy as necessary for the patient at about less than or equal to 3 g per day.

The embodiments illustrated and discussed in the specification are intended only as exemplary and the many other feasible embodiments within the scope of this invention will be readily understood and appreciated by those having ordinary skill in the art. Nothing in the specification should be construed as limiting the scope of the present invention. Many changes may be made by those having ordinary skill in the art to produce a highly effective herbal composition for diabetes and method of treatment without departing from the present invention. Accordingly, the present invention should be limited only by the claims.

I claim:

1. An herbal composition for the treatment of diabetes, comprising:
   a. 15 percent by weight of dried, powdered seeds of *Trigonella foenum-graecum;*
   b. 23 percent by weight of dried, powdered seeds of *Nigella sativa;*
   c. 10 percent by weight of dried, powdered leaves of *Origanum vulgare;*
   d. 10 percent by weight of dried, powdered sap of *Rosmarinus officinalis;*
   e. 15 percent by weight of dried, powdered beans of *Lupinus termis;*
   f. 12 percent by weight of dried, powdered black leaves of *Lawsonia inermis;* and
   g. 15 percent by weight of dried, powdered seeds of *Foeniculum vulgare.*

2. An herbal composition as claimed in claim 1 wherein the herbal composition is in non-encapsulated, powder form.

3. An herbal composition as claimed in claim 1 wherein the herbal composition is in capsule form.

4. A method of treatment for diabetes comprising:
   a. monitoring a diabetic patient's blood sugar level;
   b. administering to the patient an herbal composition comprising 15 percent by weight of dried, powdered seeds of *Trigonella foenum-graecum;* 23 percent by weight of dried, powdered seeds of *Nigella sativa;* 10 percent by weight of dried, powdered leaves of *Origanum vulgare;* 10 percent by weight of dried, powdered sap of *Rosmarinus officinalis;* 15 percent by weight of dried, powdered beans of *Lupinus termis;* 12 percent by weight of dried, powdered black leaves of *Lawsonia inermis;* and 15 percent by weight of dried, powdered seeds of *Foeniculum vulgare* in an amount of about 9 g per day for at least about 60 days until such date as the patient's blood sugar level achieves and maintains normalcy;
   c. administering to the patient the herbal composition in the amount of about 6 g per day for about another 7 days;
   d. administering to the patient the herbal composition in the amount of about 3 g per day for about another 14 days; and
   e. discontinuing administration of the herbal composition.

5. A method of treatment for diabetes comprising:
   a. monitoring a diabetic patient's blood sugar level;
   b. administering to the patient an herbal composition comprising 15 percent by weight of dried, powdered seeds of *Trigonella foenum-graecum;* 23 percent by weight of dried, powdered seeds of *Nigella sativa;* 10 percent by weight dried, powdered leaves of *Origanum vulgare;* 10 percent by weight of dried, powdered sap of *Rosmarinus officinalis;* 15 percent by weight of dried, powdered beans of *Lupinus termis;* 12 percent by weight of dried, powdered black leaves of *Lawsonia inermis;* and 15 percent by weight of dried, powdered seeds of *Foeniculum vulgare* in an amount of about 9 g per day for at least about 60 days until such date as the patient's blood sugar level achieves and maintains normalcy;

c. administering to the patient the herbal composition in the amount of about 6 g per day for about another 7 days;

d. administering to the patient the herbal composition in the amount of about 3 g per day for about another 14 days; and e. continuing administration of the herbal composition as necessary for the patient at about less than or equal to 3 g per day of the herbal composition.

6. A method of treatment for diabetes as claimed in claim 4, wherein the herbal composition administered in steps (b) through (e) is administered to the patient in three equivalent dosages which are one third of the amount of a total daily dosage, each dosage being administered in succession in approximately even intervals of about 5 hours each throughout a day, a first dosage being administered about 30 minutes to about 45 minutes prior to food ingestion, a second dosage and third dosage being administered prior to, with, or after food ingestion.

7. A method of treatment for diabetes as claimed in claim 5, wherein the herbal composition administered in steps (b) through (e) is administered to the patient in three equivalent dosages which are one third of the amount of a total daily dosage, each dosage being administered in succession in approximately even intervals of about 5 hours each throughout a day, a first dosage being administered about 30 minutes to about 45 minutes prior to food ingestion, a second dosage and a third dosage being administered prior to, with, or after food ingestion.

* * * * *